United States Patent
Nietfeld

(10) Patent No.: US 7,328,110 B2
(45) Date of Patent: Feb. 5, 2008

(54) SYSTEM FOR CELLULAR STORAGE AND GENETIC INFORMATION RETRIEVAL

(75) Inventor: Jan Jaap Nietfeld, Maarssen (NL)

(73) Assignee: BioTech Holding B.V., Naarden (NL)

( * ) Notice: Subject to any disclaimer, the term of this patent is extended or adjusted under 35 U.S.C. 154(b) by 0 days.

(21) Appl. No.: 10/474,385

(22) PCT Filed: Apr. 9, 2002

(86) PCT No.: PCT/IB02/02271

§ 371 (c)(1),
(2), (4) Date: May 13, 2004

(87) PCT Pub. No.: WO02/094439

PCT Pub. Date: Nov. 28, 2002

(65) Prior Publication Data

US 2004/0185427 A1 Sep. 23, 2004
US 2005/0164157 A9 Jul. 28, 2005

Related U.S. Application Data

(60) Provisional application No. 60/282,742, filed on Apr. 10, 2001.

(51) Int. Cl.
*G06F 7/00* (2006.01)
(52) U.S. Cl. ............... 702/19; 702/20; 703/11; 707/102; 435/5; 435/6; 435/7.1
(58) Field of Classification Search ............ 435/6; 702/20, 179, 19
See application file for complete search history.

(56) References Cited

U.S. PATENT DOCUMENTS 5,993,387 A 11/1999 Moore et al.
6,291,182 B1* 9/2001 Schork et al. ............ 435/6
2003/0108905 A1* 6/2003 Nietfeld .................. 435/6

FOREIGN PATENT DOCUMENTS

WO WO 91/09521 7/1991
WO WO01/70023 A1 9/2001

OTHER PUBLICATIONS

Cargill, et.al., Nature Genetics, 22(3):231-138 (1999).*
Cole, et.al., Am. J. Hum. Genet., 44:835-843 (1989).*
"Idgene Pharmaceuticals Overview"—cited in Written Opinion of International Preliminary Examining Authority, Apr. 7, 2001.
"LifeSeq Gold Gene Database"—cited in International Search report, Dec. 13, 2000, p. 1-4.
Philipkoski, Kristen: "Shopping for Single Genes"—cited in International Search Report, Mar. 24, 2000, p. 1-2.
Gannon, Pamela M.: "Genes on the Web: A Report from the Internet & Society 2000 Conference" —cited in the International Search Report, Apr. 4, 2001.
European Patent Office Communication, Application No. 02735860.5, Sep. 15, 2005, 5 pages.

* cited by examiner

*Primary Examiner*—Mary K Zeman
(74) *Attorney, Agent, or Firm*—Wood, Phillips, Katz, Clark & Mortimer

(57) ABSTRACT

A system for storage of cellular material and retrieval of genetic information comprises a cell bank comprising a plurality of cell storage units for storage of cellular material from individual depositors. Cryo-preservation of the material is contemplated. Genetic information obtained from the cellular material is complied in a digital information which can be accessed such as for medical, pharmaceutical, and biological research, diagnosis, and treatment. Fees generated in connection with retrieval of the genetic information will permit cost-effective storage of cellular material. When a decrease in storage costs and storage fees leads to an increase in the number of depositions of cellular material, the significance and the value of the genetic information available in the data base will increase.

6 Claims, 1 Drawing Sheet

SYSTEM FOR CELLULAR STORAGE AND GENETIC INFORMATION RETRIEVAL

CROSS-REFERENCE TO RELATED APPLICATIONS

This application is the U.S. national phase of International Application Ser. No. PCT/IB02/02271, which was filed on Apr. 9, 2002, and claims the benefit of U.S. Provisional Application No. 60/282,742, which was filed on Apr. 10, 2001.

TECHNICAL FIELD

The present invention relates generally to a system for storage of cellular material, and more particularly to a system for cryogenic storage of cellular material and for retrieval of digital, genetic information obtained from the cellular material, thus facilitating dissemination of the retrieved information such as for research, biomedical and pharmaceutical research, diagnosis and medical treatment. The present system contemplates that sale of the genetic information, such as by subscription of users to the system provides funds to facilitate storage of the cellular material.

BACKGROUND OF THE INVENTION

Cell banking is a service industry in which live cells are stored for later use. This type of storage of cellular material has been practiced for a number of years, as exemplified by the storage of bovine sperm cells for artificial insemination of cows, which has been practiced for several decades.

Presently, many types of cells, from fungi to human cells, are stored for varying periods of time, till the use of the cells is required, such as for research, production of bio-active molecules, diagnosis, or medical treatment. A well-known method for long-term storage of cells, while maintaining their viability, is cryo-preservation. Such preservation is effected by freezing and cooling the cells, along a prescribed path, to a temperature on the order of $-196°$ C., in the presence of compounds which render the cells resistant to frost damage. After such a procedure, maintaining the cells at such a low temperature prevents deterioration of the cellular material.

With the technical advances that are being made in biomedical research and tissue engineering, it is being recognized that many possibilities may exist for use of human stem cells for various replacement therapies. These developments have led to a growing demand for facilities where stem cells of individuals can be isolated, cryo-preserved, and stored for later (autologous) use. By way of example, the desirability of storing the cord blood stem cells of newborns, is becoming increasingly recognized, with a rapidly increasing number of deposits of such stem cells in private cell banks.

Because of the rapid progress in biomedical sciences, an increasing number of applications are being found for use of cellular material in medical treatments. Moreover, it is expected that the potential of "tissue engineering" in the future may lead to the "re-growth" of organs from stem cells. This would address the growing shortage in donor material for transplants, and could potentially result in large savings in healthcare costs. It is believed that such developments will create an increased demand for storage facilities for cells or tissue, either for relatively short periods of time such as for the depositor's benefit, or for longer time periods so as to benefit the depositors, other individuals (such as family members), selected groups in society, and society as a whole, by use of the material for medical treatment and/or research.

It has been recognized that private cell banking can be a potentially profitable business, with the recognition that virtually anyone could be a potential client of such services in view of the potential benefits that could be derived. However, it is recognized that the relatively high fees and expenses associated with private cell banking substantially prevents a relatively high percentage of market penetration, particularly in less affluent societies.

In accordance with the present invention, it is recognized that cell banking market penetration could be significantly enhanced if fees and expenses associated therewith could be moderated, thus enhancing overall, global market penetration. Of course, the ability of a cell banking facility to control and moderate expenses facilitates competition with other like storage facilities.

SUMMARY Of The INVENTION

The present invention contemplates a system for cellular material storage, i.e., cell banking, and genetic information retrieval, whereby fees generated in connection with the storage of retrieved information facilitates cost-effective cell storage. By this system, it is contemplated that increasingly large numbers of cell samples may be efficiently and cost-effectively stored, with the genetic information obtained from the cellular material creating a highly valuable data base from which information can be retrieved for medical, pharmaceutical, and biological research, diagnosis, and treatment.

The system embodying the principles of the present invention comprises a cell bank comprising a plurality of cell storage units for storage of cellular material. Typically, such cell storage is effected by cryo-preservation, but it is within the purview of the present invention that alternative storage techniques can be employed.

The present system further includes a digital information unit for digitally storing genetic information obtained from the cellular material stored in the cell storage units. The digital information unit preferably comprises at least one digital computer having sufficient digital storage capacity for storage of the potentially vast amounts of genetic information obtained from the stored cellular material.

The present system further comprises an arrangement for digital data retrieval interfaced with the digital information unit for retrieving selected genetic information stored in the digital information unit The data retrieval arrangement may be integrated with the digital computer. Remote access of the digital information via the telephone, the Internet, or by like means, enhances the value of the stored digital information by permitting rapid and convenient access of the information on a global basis.

The present invention contemplates that the expenses associated with stored cellular material can be recouped through subscription or like fees paid by users who access the stored genetic information. Because such genetic information is potentially quite valuable, such as for research, diagnosis, and treatment, payment for such potentially unique information will be highly cost-effective in comparison to previously-known techniques. As a consequence, expenses associated with cell storage can be increasingly covered by fees paid for data retrieval thus desirably increasing the use of such cell storage, which in turn enhances the depth, and resultant value, of the genetic information data base.

DETAILED DESCRIPTION

Figure 1:
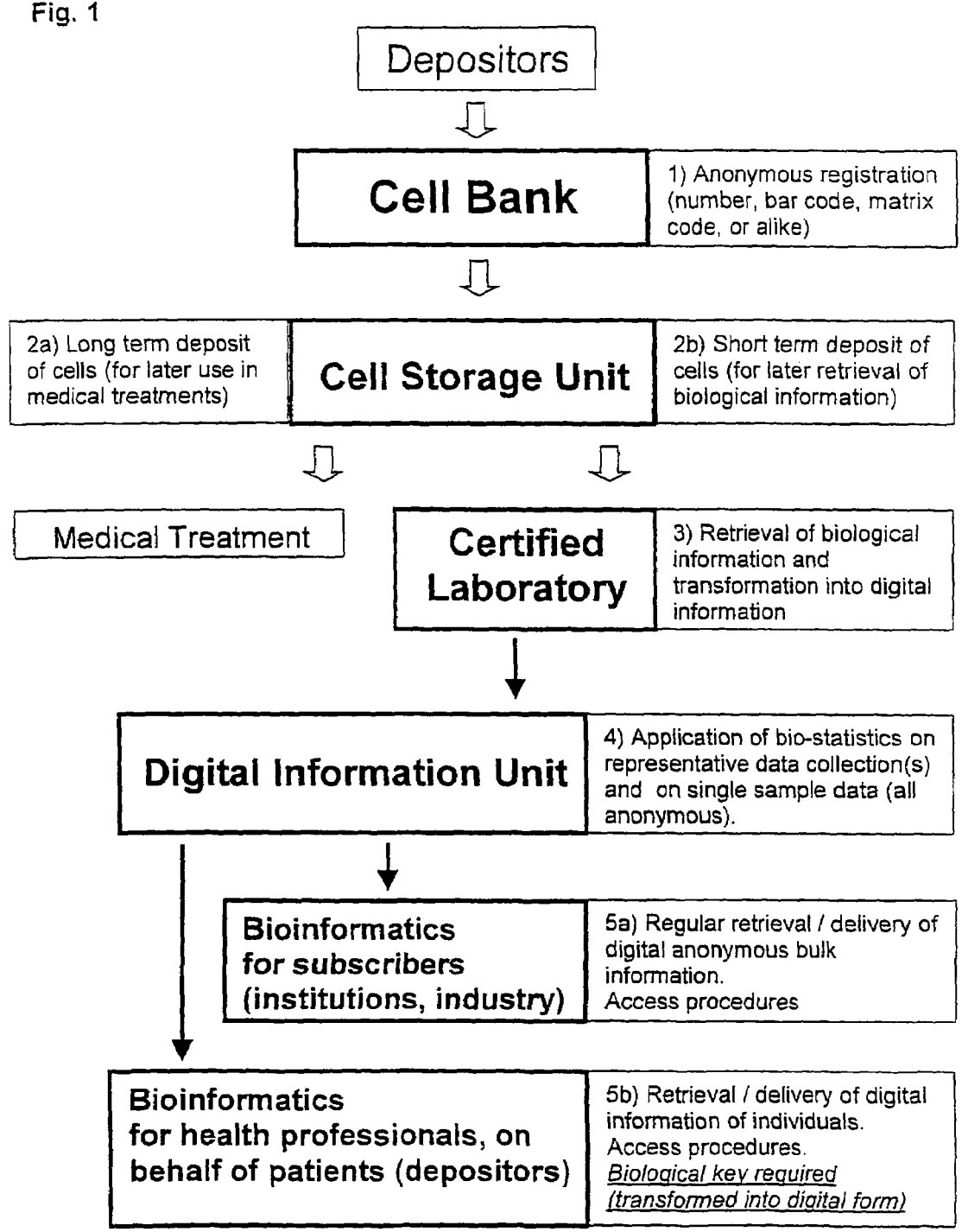
FIG. 1 is a flow diagram illustrating a system for cell storage and data retrieval embodying the principles of the present invention.

While the present invention is susceptible of embodiment in various forms, there is shown in the drawing, and will hereinafter be described, a presently preferred embodiment, with the understanding that the present disclosure is to be considered as an exemplification of the invention, and is not intended to limit the invention to the specific embodiment illustrated.

Because of the recent progress in the research of the human genome, the elucidation of information about genetic predisposition of diseases is rapidly growing at the moment, and is expected to expand explosively in the near future. This development enables population-wide bio-statistics on the basis of such genetic information, and the production of an increasingly valuable collection of bio-informatics, leading to population-wide prognostic health profiles, and the practice of prognostic medicine. As will be appreciated, the generation of such bio-informatics depends upon the collection of a statistically significant number of samples from the population, for subsequent retrieval of the desired genetic information.

The highest value of this type of bio-informatics (in relation to healthcare and socio-economics) is gained if the underlying data are available as early as possible. This dictates the retrieval of predisposing genetic information preferably take place using biological material from individuals around the time of birth This can be achieved by using rest cells, which remain after isolation of the stem cells from umbilical cord blood, or by using a small fraction of the stem cells themselves. Typically, the stem cells are stored in private cell banks, as discussed hereinabove, for new-born depositors. However, it is recognized that biological material deposited at later ages can also provide valuable genetic information which can be retrieved, and contribute to a collection of bio-informatics.

For the protection of the privacy of individual depositors, the rest cells (or other cellular material to be screened for predisposing genetic information) will be used on an anonymous basis, with no reference being kept linking the rest cells or other cellular material to the depositor, and only after the informed consent of the depositors, or their legal representatives.

FIG. 1 illustrates the present system for storage of cellular material and genetic information retrieval. Cells from individual depositors are received by a cell bank of the system, with anonymous registration by means of bar code, matrix code, or the like being effected.

The cellular material received in the cell bank is stored in a plurality of cell storage units of the bank for individualized storage of the collected cellular material. While the present system principally contemplates the use of short term stored cellular material for creation of a digital genetic information data base, long term deposit of cells can be effected for use of the endogenous biological information, and associated medical treatment. Cryogenic preservation of the cellular material is presently contemplated, but other preservation techniques can be alternatively employed to preserve the cellular material for data collection.

The creation of a data base of genetic information, in accordance with the present system, is typically effected by suitable laboratory procedures, which transform the biological information obtained from the cellular material into digital information The digital information, in turn, is stored in a digital information unit of the system, which typically comprises a suitable digital computer or like apparatus.

The genetic information stored in the digital information unit can be evaluated by the application of bio-statistics, thus facilitating retrieval of the information as may be required for biomedical research, pharmaceutical research, diagnosis, treatment and prognostic health care. A suitable data retrieval arrangement is interfaced with the digital information unit, and may be incorporated therein, whereby selected genetic information can be retrieved.

As illustrated, it is contemplated that the resultant bio-informatics can be retrieved and used in various fashions. For example, subscribers to the present system may retrieve the bio-informatic data as anonymous bulk information, as may be desired for medical research It is contemplated that bio-informatic data may be accessed and retrieved by health-care professionals, such as on behalf of individuals, to facilitate medical diagnosis and treatment. Use of a biological key, in digital form, will be required for retrieval of up to that point strictly anonymous individual genetic information, thus assuring the privacy of individual depositors whose cellular material has been contributed to the system.

As noted above, it is contemplated that revenue generated from the supply of bio-informatic data will facilitate storage of the cellular material from which the genetic data is obtained. As noted, clients for collected, anonymous information will typically be healthcare institutes, and bio-medical and bio-technological companies. It is further contemplated that users of such collected anonymous data will include various local and national governmental organizations, insurance companies, and pharmaceutical companies, as well as other suppliers of drugs aid other medical devices for the benefit of diseased and/or disabled individuals.

It is further contemplated that other types of clients will be found among individual patients having an interest in the information based on their own stored cellular material. For diagnostic purposes, or in the course of medical treatment, it can be of crucial importance for an individual patient and the consulting physician to have access to genetic information that is gathered based on the biological material of that particular individual. While it is contemplated that the present system would collect cellular material for data base creation on an anonymous basis, it is contemplated that a biological coding system, such as disclosed in patent application Serial No. PCT/NL01/00160, filed 26 Feb. 2001 (with a priority date of 25 Feb. 2000, based on the Dutch patent application No. 1014491, filed that day in the Netherlands), hereby incorporated by reference, can be employed to permit an individual to access the otherwise anonymous information generated from the cellular material of that particular patient.

As will be appreciated, the registration, handling, and storage of human cells (or tissue) or the biomedical information retrieved therefrom, are typically subject to relatively strict regulations, particularly intended to maintain the privacy of depositors, and ensure the confidentiality of the bio-medical information based on the cellular material. This requires that either personal data be separated from the cellular material (and the biomedical information), in a secured fashion, or that the biomedical information be made anonymous at some stage so that it can no longer be associated with the depositor of the cellular material. As will be appreciated, such restrictive regulations are intended to avoid ethical and legal issues that could result from non-anonymous biomedical information use. It is recognized, for example, that non-anonymous access to such information could undesirably result in discrimination toward depositors of such material by their employers, insurance companies, or other entities. Of course, during very long-term storage of cellular material, individual depositors are likely to have little control over the material, or the bio-medical information derived therefrom, with the security of the material and the biomedical information resting in the hands of the registration and/or storage facility.

Apart from the disease-linked genetic information that will be retrieved and made available in the marketplace according to the bio-informatics data base of the present invention, it is further contemplated that the present invention will provide opportunities, especially to pharmaceutical companies, to have the collection of cellular material screened for one or more genetic target sequences not directly linked to a disease itself, but which would be potentially valuable for such a company in development of new drugs or treatments. Such a new drug could have a direct regulatory interaction (inhibitory or stimulatory) with the target locus on DNA (or RNA) in diseased cells.

While it is recognized that cellular material could be stored without any registration of associated personal data, this would make it impossible for depositors to ever reclaim the deposited material, or obtain access to the biomedical information obtained from the material. Thus, the present system contemplates that while retrieved bio-informatic data will ordinarily be fully anonymous, certain procedures will permit a depositor of cellular material to reclaim the material and/or obtain access to the retrieved biomedical information.

From the foregoing, numerous modifications and variations can be effected without departing from the true spirit and scope of the novel concept of the present invention. It is to be understood that no limitation with respect to the specific embodiment disclosed herein is intended or should be inferred. The disclosure is intended to cover, by the appended claims, all such modifications as fall within the scope of the claims.

What is claimed is:

1. A method for cellular material storage and genetic information retrieval and dispersal in an efficient and cost effective manner, comprising the steps of:
   (a) collecting samples of cellular material and delivering said samples to a cell bank, which comprises a plurality of cell storage units for storage of cellular material,
   (b) splitting the samples into portions, one portion of each sample being stored in a cell storage unit so that the viability is preserved, and another portion of each sample being used for retrieval of genetic information,
   (c) retrieving the genetic information from the sample portion used for retrieval of genetic information and digitally storing said genetic information in a digital information unit,
   (d) retrieving the stored genetic information from the digital information unit by a suitable data retrieval arrangement interfaced with the digital information unit,
   (e) evaluating the sample data collection created from the stored information by the application of statistics, leading to the bioinformatics data required for in at least one of the following areas: (I) bio-medical research, (II) pharmaceutical research, (III) genetic target screening, (IV) diagnostics, (V) treatment, and (VI) prognostic healthcare,
   (f) storing the resulting bioinformatics data in the digital information unit, and
   (g) retrieving the bioinformatics data from the digital information unit by data retrieval means interfaced with the digital information unit.

2. The method according to claim 1, wherein the storage method comprises cryopreservation.

3. The method according to claim 1, wherein a digital computer is used as the digital information unit.

4. The method according to claim 1, wherein the data retrieval means is operatively interconnected with telephone or internet access.

5. The method according to claim 1, wherein the digitally stored information is stored anonymously and individual data are accessible by using a biological coding system.

6. The method according to claim 1, wherein the sample data collection is evaluated statistically with respect to genetic predisposition for diseases.

* * * * *